Feb. 4, 1964 C. FISCHER Plant Pat. 2,351
GLADIOLUS PLANT
Filed Oct. 16, 1962
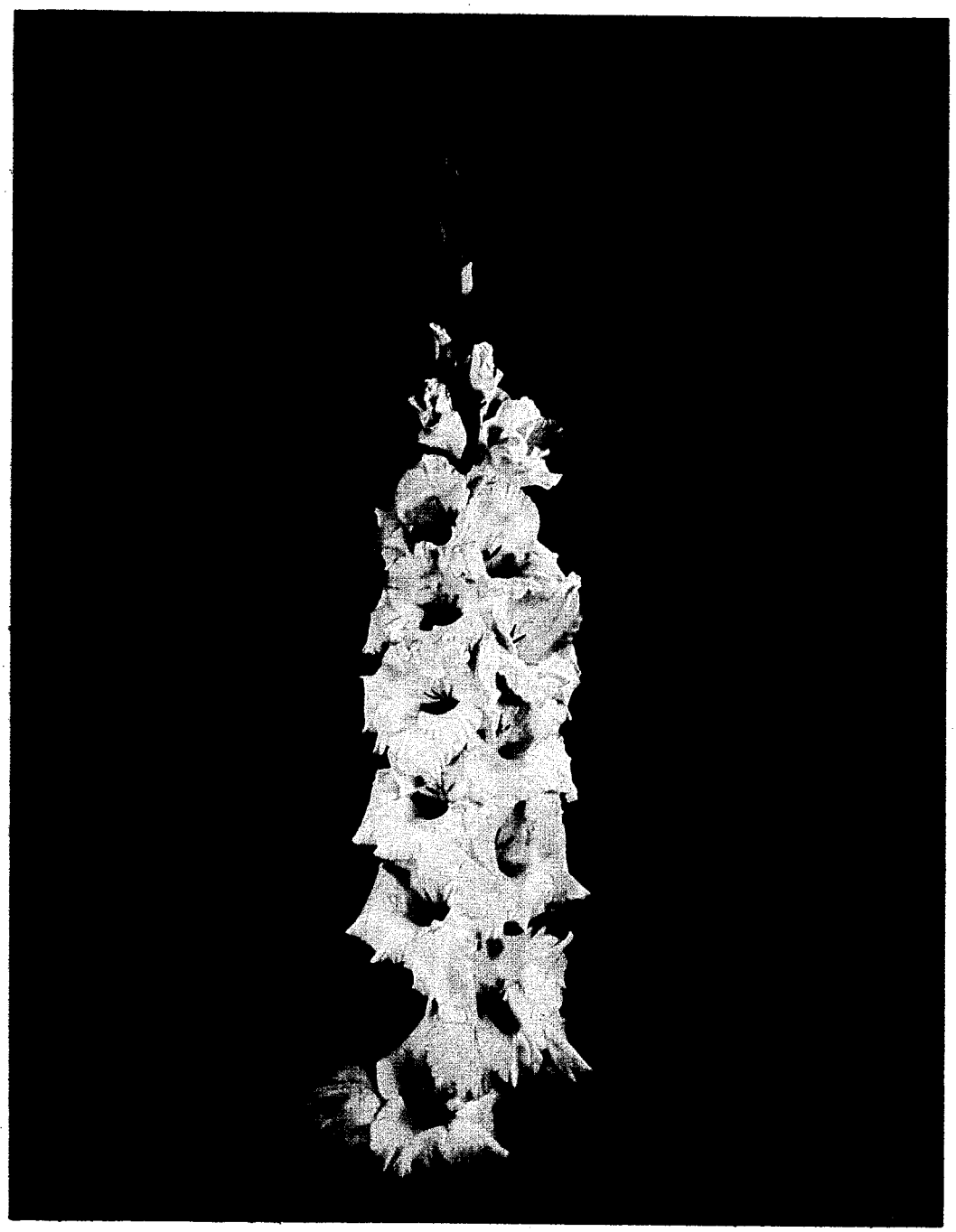
Inventor.
Carl Fischer
By: Robb & Robb
Attorneys United States Patent Office Plant Pat. 2,351
Patented Feb. 4, 1964

2,351
GLADIOLUS PLANT

Carl Fischer, St. Charles, Minn., assignor to Imperial Flowers Limited, Leamington, Ontario, Canada, a corporation of Canada Filed Oct. 16, 1962, Ser. No. 231,049
1 Claim. (Cl. Plt.—85)

The present invention relates to a new and distinct variety of gladiolus plant which was originated by me by crossing two unnamed and unpatented gladiolus varieties of unidentified parentage, said cross having been made by me by manual cross-pollination in my breeding fields at St. Charles, Minnesota.

As the result of this breeding, I have produced a new and improved gladiolus variety having a unique combination of characteristics which distinguish it from its parents, as well as from all other varieties of which I am aware, as evidenced by the following features which are outstanding therein:

(1) A double row arrangement of the florets on the flower stems;

(2) The ability of the florets to open well from tight buds;

(3) The large number of florets which open at one time;

(4) Good temperature resistance to both heat and cold; and (5) A distinctive and attractive chalky white general color tonality of the flowers.

My new variety is quite distinct from and a definite improvement over other white gladiolus varieties by virtue of the formal double row arrangement of the florets on the stems, greater ability to open well from tight buds, relatively more florets opening at once in the field, with as many as from 10 to 12 florets opening at one time in each flower head, and better temperature tolerance with consequent ability to grow well under conditions of both heat and cold.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Vigorous; prolific propagator; average height ranges from about 60 inches to 64 inches.

Blooming habit: Mid-season bloomer in the northern latitudes of the United States; comes into bloom from large bulbs in about 85 days; from 10 to 12 florets open at one time, with successive openings of additional florets until a total of from 20 to 24 florets open on each spike.

Stems: Very straight; stiff.
- *Diameter at base.*—About ½ inch.
- *Color (just above bulb).*—Orchid Purple, Plate 31/3.

Foliage: Droopy; leaves average from about 30 inches to 34 inches tall, and range from about 1½ inches to 1¾ inches wide. Color—deep green.

Disease resistance: Unusually good resistance to Fusarium yellows, Sclerotina dry rot and Septoria leaf spot, as determined by comparison with other varieties grown in my fields near St. Charles, Minnesota, in irrigated black loam soil.

Corms (bulbs): Healthy; plump; very smooth; average about 2 inches in diameter; thin husks hug the corm tightly and have a rose-purple cast. Color of flesh—Chrome Yellow, Plate 605/2.

*Flower*

Spike: Tall; slender; bears from 20 to 24 buds, with from 4 to 6 florets opening the first day and thereafter with from 10 to 12 florets opening at one time while first florets are still fresh, and with from 6 to 8 buds showing color above the open florets.

Bud:
- *Size.*—About 2½ inches long when opening.
- *Opening.*—Opens well; all buds will open after several days.

Flower:
- *Arrangement.*—Florets are formally arranged in a double row on the stem and all face in the same direction.
- *Size.*—Lower florets average from 4½ inches to 5 inches in diameter when permitted to bloom on the plant in the field, while upper florets are progressively smaller.
- *Form.*—Wide open; recurved; ruffled.
- *Keeping qualities.*—Keeps well.

Petals:
- *Shape.*—Round; ruffled; occasionally needle-pointed.
- *Size.*—Upper petals—about 2¼ inches wide. Lower petals—about 1½ inches wide.
- *Aspect.*—Average substance; smooth surface.
- *Fragrance.*—None.
- *Color.*—Chalky white, with reverse surfaces of petals having small streaks at calyx ranging from Roseine Purple, Plate 629/3 to Roseine Purple, Plate 629/2, and with calyx being Roseine Purple, Plate 629/1.

*Reproductive Organs*

Stamens: Color—purple.

Pistil: Color—white.

I claim:

A new and distinct variety of gladiolus plant, substantially as herein shown and described, characterized particularly as to novelty by the unique combination of a double row arrangement of the florets on the flower stems, the ability of the florets to open well from tight buds, a habit of opening of the florets in an exceptionally large number at one time, good temperature tolerance to both heat and cold, and a distinctive and attractive chalky white general color tonality of the flowers.

No references cited.